(12) United States Patent
Pansiera

(10) Patent No.: US 6,764,244 B2
(45) Date of Patent: Jul. 20, 2004

(54) PIN STOP FOR MECHANICAL JOINTS

(76) Inventor: Timothy Thomas Pansiera, 31 Teaberry La., Weaverville, NC (US) 28787

( * ) Notice: Subject to any disclaimer, the term of this patent is extended or adjusted under 35 U.S.C. 154(b) by 0 days.

(21) Appl. No.: 10/265,929

(22) Filed: Oct. 7, 2002

(65) Prior Publication Data
US 2004/0067095 A1 Apr. 8, 2004

(51) Int. Cl.⁷ ................................................. F16B 7/10
(52) U.S. Cl. ....................... 403/102; 403/112; 403/113; 403/161; 623/43; 623/44; 602/16
(58) Field of Search ............................. 403/73, 83, 84, 403/91, 93, 100–102, 105, 112, 113, 117, 322.4, 109.6, 161, 315–319, 62; 623/322.4, 39, 41, 43, 44; 602/16

(56) References Cited

U.S. PATENT DOCUMENTS

| | | | | |
|---|---|---|---|---|
| 2,747,283 A | * | 5/1956 | Sanders | 33/439 |
| 4,502,472 A | * | 3/1985 | Pansiera | 602/16 |
| 4,997,449 A | * | 3/1991 | Prahl et al. | 623/44 |
| 5,022,390 A | | 6/1991 | Whiteside | |
| 5,779,735 A | * | 7/1998 | Molino | 623/44 |
| 6,113,642 A | * | 9/2000 | Petrofsky et al. | 623/44 |
| 6,613,097 B1 | * | 9/2003 | Cooper | 623/44 |

* cited by examiner

Primary Examiner—Anthony Knight
Assistant Examiner—Victor MacArthur
(74) Attorney, Agent, or Firm—Dorothy S. Morse

(57) ABSTRACT

A compact and efficient stop for establishing the position of maximum extension in a mechanical joint, which comprises a free-floating piston, a piston-retaining pin, and a resilient bumper positioned to engage one end of the piston. The piston, retaining pin, and bumper are located on one side of the joint. A cross stop bushing on the opposing side of the mechanical joint is positioned to engage the exposed end of the piston when the joint is in its position of maximum extension. Applications may include, but are not limited to, use in orthotic and prosthetic devices wherein a larger tolerance in the range of motion is provided for a locking mechanism to engage as the joint reaches maximum extension, while any unwanted feeling of free movement in the joint at full extension is concurrently dampened. A secondary advantage is a softer extension stop for a user.

20 Claims, 5 Drawing Sheets

PIN STOP FOR MECHANICAL JOINTS

CROSS-REFERENCES TO RELATED APPLICATIONS

None

BACKGROUND

1. Field of the Invention

This invention relates to stops for mechanical joints, specifically to a compact, efficient, and comfort enhancing means for defining a position of maximum extension in a mechanical joint, which dampens free movement in the joint as maximum extension is reached. When the pin stop present invention is used in orthotic and prosthetic devices, to support a knee, it is contemplated for the joints in which the pin stop present invention is used to also have a locking mechanism that when engaged prevents further flexion in the associated joint while concurrently allowing needed extension in incremental amounts until the position of maximum extension defined by the present invention is reached. The pin stop invention comprises a free-floating piston having an interior end and a partially exposed exterior end, a resilient bumper positioned to engage the interior end of the piston during maximum joint extension, and a piston-retaining pin, all of which are contained laterally within the perimeter structure of one of the pivoting members in a mechanical joint so that the exterior end of the piston is able to engage a cross stop bushing laterally positioned within the perimeter structure of the other pivoting member in the joint when the joint is at or very near to its position of maximum extension. Applications may include, but are not limited to, use in orthotic and prosthetic devices whereby the pin stop invention would assure a larger tolerance in the range of motion provided for the locking mechanism to engage as the joint with which it is associated nears its position of maximum extension, while dampening any unwanted feeling of free movement. A secondary advantage provided by the pin stop invention in orthotic and prosthetic applications is a softer extension stop for a user. However, it is contemplated that application in any mechanical joint for which the compact configuration and/or dampening action of the present pin stop invention would provide some assistance or technical advantage, would be within the scope of the pin stop invention.

2. Description of the Related Art

Components used in orthotic and prosthetic devices should be compact and minimally obtrusive for ease of use, enhanced social acceptability, and a lessened risk of hazard or damage during use. Further, a user should not experience insecurity, discomfort, or apprehension as a result of any aspect of their performance. As a fundamental part of their construction, all mechanical joints used in orthotic and prosthetic devices, must include design features and/or apparatus that define the limits of their flexion and extension. Often, the means used for defining maximum joint extension is bulky in configuration, provides an abrupt stop for the user, and/or adds unwanted thickness dimension to the device, such as the invention disclosed in U.S. Pat. No. 5,022,390 to Whiteside (1991), wherein the means for limiting extension of the ankle joint in a device supporting a leg and foot comprises an adjustable stop, mounting block, and abutment combination positioned against the outside surface of the leg support, behind the ankle of its user. In contrast, the extension limiting means of the present invention is more compact than that in the Whiteside invention, and it is laterally contained within the perimeter structure of an associated mechanical joint where it is protected from and less likely to fail as a result of unwanted interaction with surrounding objects. Further, the present invention also assures a larger tolerance in the range of motion provided for the locking mechanism to engage as it reaches the position of maximum extension than does the Whiteside invention, providing a softer extension stop for the user and dampening of any unwanted feeling of free movement in the joint. In addition to orthotic and prosthetic use, it is also contemplated for the present invention to be used in any industrial application requiring a mechanical joint with a compact configuration or dampening action, wherein some functional assistance or an operational advantage is provided by use of such configuration or dampening capability, or combination thereof. No means for limiting the maximum extension of mechanical joints is known to have the same structure or all of the advantages of the present pin stop invention.

BRIEF SUMMARY OF INVENTION

It is the primary object of this invention to provide a compact means for limiting the maximum extension of a mechanical joint. It is also an object of this invention to provide a means for limiting the maximum extension of a mechanical joint that is substantially positioned within the pivoting members of the joint to protect it from and make it less likely to fail as a result of unwanted interaction with surrounding objects. It is a further object of this invention to provide a means for limiting the maximum extension of a mechanical joint that assures a larger tolerance in the range of motion provided for an associated locking mechanism to engage as the joint reaches its position of maximum extension, while dampening any unwanted feeling of free movement in the joint. A further object of this invention is to provide a means for limiting the maximum extension of a mechanical joint that is a softer extension stop for the user. It is also an object of this invention to provide a means for limiting the maximum extension of a mechanical joint that is simple in design and requires little or no maintenance. A further object of this invention is to provide a means for limiting the maximum extension of a mechanical joint that is made from durable materials and is efficient in operation. It is also an object of this invention to provide an extension limiting means for mechanical joints that has sufficient strength for use in orthotic devices, such as those employed to support a human knee. It is a further object of this invention to provide a means for limiting the maximum extension of a mechanical joint that is easy and cost efficient to manufacture.

As described herein, properly manufactured, and connected between the paired pivoting members of a mechanical joint, the pin stop of the present invention provides a means for defining the maximum extension of one member of the joint relative to the other. A piston is inserted into a longitudinal bore within one of the pivoting members, where it remains laterally contained within the perimeter structure of the pivoting member on the outside portion of the mechanical joint's pivoting axis. The piston remains free-floating within the bore, but is not freely removable from it. A cutout area or opening centrally in the piston accommodates a transversely positioned retaining pin that allows the piston a limited amount of longitudinal movement within the bore, yet retains the piston substantially within the bore, with only a small portion of the piston's exterior end remaining exposed beyond the bore's open end. A resilient bumper is positioned within the closed end of the bore, and engages the interior end of the piston when the pivoting members are rotated into a position of maximum extension. In this way the present invention assures a larger tolerance in the range of motion provided for an associated locking mechanism to engage as the joint reaches its position of maximum extension, while dampening any unwanted feeling of free movement in the joint. It also provides a softer extension stop for the user. When flexion occurs in the mechanical joint to which the present invention is connected, the portion of the piston extending beyond the open end of the bore can be hand-manipulated to move a fractional distance in and out of the bore, but cannot be removed from the bore unless the retaining pin is first withdrawn. Preferably the design of the mechanical joint is such that the retaining pin is not visible or accessible, unless the pivoting members are physically separated from one another. For use as a means of limiting the maximum extension of the pivoting members in a mechanical joint, the present invention must also include a component connected to the second pivoting member and configured to engage the exposed end of the piston as the joint reaches maximum extension. Such engagement means in the most preferred embodiment of the present invention is provided in the form of a cross stop bushing that is laterally contained within the second pivoting member. As the pivoting members near a position of maximum extension relative to one another, the side of the cross stop bushing that is facing the piston is moved against the exposed end of the piston, causing the interior end of the piston to move toward the closed end of the bore until it becomes firmly positioned against the resilient bumper in the bottom of the bore. When a locking mechanism, such as a ratchet assembly, is used in the joint to prevent flexion and maintain the joint in its position of maximum extension, as maximum extension is reached, the bushing, piston, and bumper all become pressed firmly against one another. After the ratchet assembly or other locking means is released and flexion occurs, the bushing becomes separated from the exposed end of the piston. The piston remains within the bore where it will be ready for subsequent engagement with the cross stop bushing, however it is again free-floating and easily movable away from the bumper. The present invention has few components, each of simple design, which can be easily and cost efficiently manufactured and assembled. When the piston and cross stop bushing are made from stainless steel, the pin stop invention is durable and has sufficient strength to provide proper support for prosthetic and orthotic devices. Further, the compact design of the present invention allows it to remain laterally contained within the perimeter structure of the pivoting members of the joint with which it is associated where it is protected from and less likely to fail as a result of unwanted contact with surrounding objects.

While the description herein provides preferred embodiments of the present invention, it should not be used to limit its scope. For example, variations of the present invention, while not shown and described herein, can also be considered within the scope of the present invention, such as variations in the length or diameter dimensions of the piston, the thickness dimension and configuration of the resilient bumper, the number of bumpers used, the material from which the bumper or bumpers are made, the configuration of the central portion of the piston that interacts with the retaining pin for piston retention within the bore, the diameter dimension of the retaining pin, whether threads are used to secure the retaining pin in its usable position, and the end configuration of the retaining pin that could be designed to allow insertion of a tool therein to provide easy removal of the retaining pin for access to the piston and bumper. Thus the scope of the present invention should be determined by the appended claims and their legal equivalents, rather than being limited to the examples given.

DETAILED DESCRIPTION OF THE INVENTION

Figure 1:
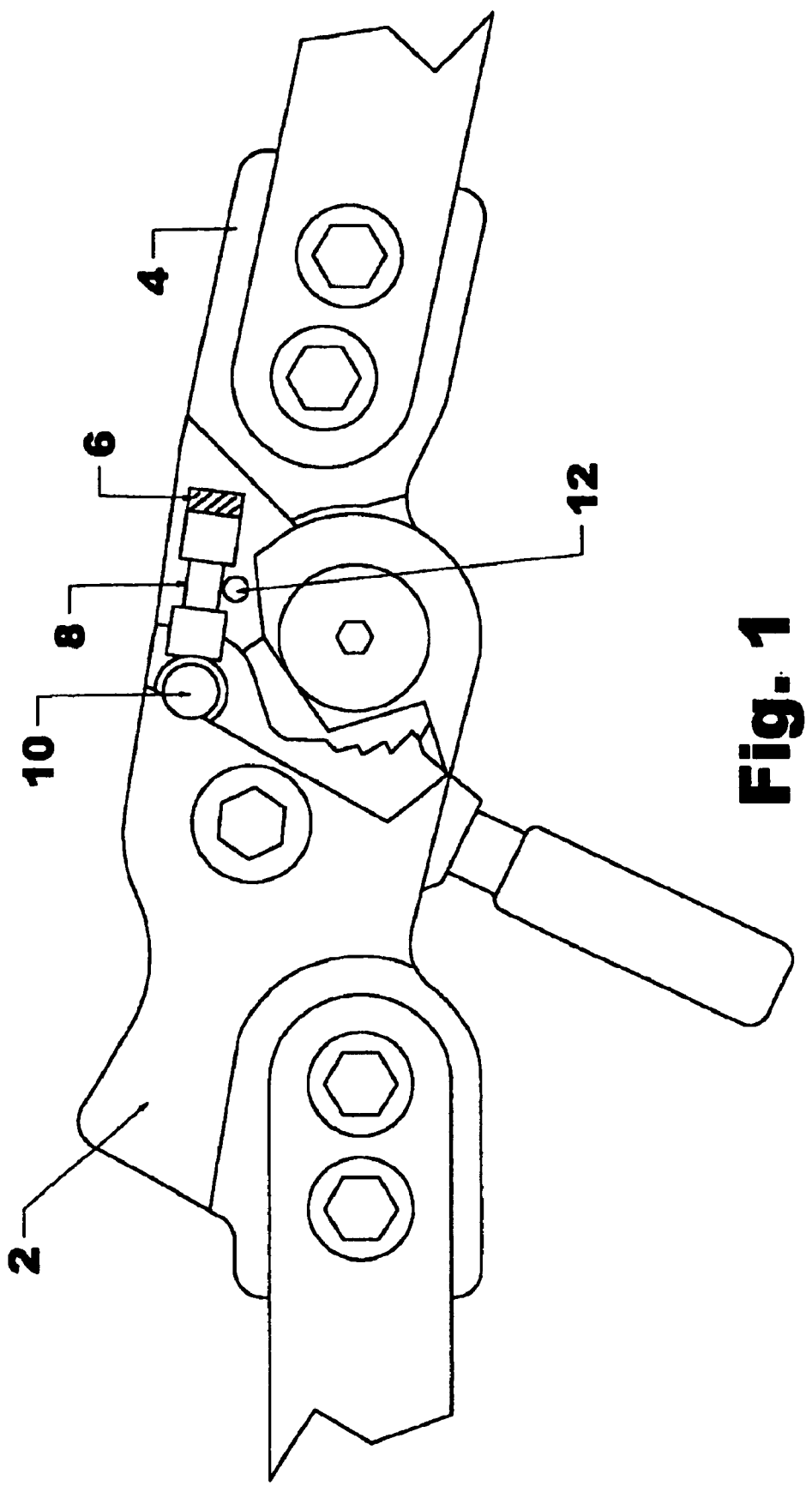
FIG. 1 is a side view of the most preferred embodiment of the present invention with its components laterally contained within a mechanical joint and located so as to limit joint extension, with the mechanical joint shown locked at its position of maximum extension, and also with the interior end of its piston in contact with a resilient bumper and the piston and bumper connected to the same one of the pivoting members in the mechanical joint, and the exposed end of the piston in contact with a cross stop bushing connected to the other pivoting member in the mechanical joint.

FIGS. 1–8 show the most preferred embodiment of the present invention having a piston 8, a retaining pin 12, a bumper 6, and a cross stop bushing 10, all positioned relative to one another so as to define the maximum extension allowable between a first pivoting member 2 and a second pivoting member 4 in a mechanical joint. In orthotic and prosthetic devices, the most preferred embodiment assures a larger tolerance in the range of motion provided for a locking mechanism to engage as first pivoting member 2 and second pivoting member 4 move into their positions of maximum extension, while dampening any unwanted feeling of free movement of one pivoting member relative to the other. A secondary advantage provided by the most preferred embodiment of the present invention in orthotic and prosthetic use is a softer extension stop for a user. However, use of the present invention is contemplated for any mechanical joint in which the compact configuration and/or dampening action of the present pin stop invention would provide some assistance or technical advantage. FIGS. 1, 5, 6, 7, and 8 also show an unnumbered ratchet assembly with a downwardly extending handle (also unnumbered), which is not part of the invention, usable for locking the mechanical joint against flexion while at the same time allowing further extension in defined increments until the position of maximum extension for the joint is achieved. The handle of the ratchet assembly can be moved into a position whereby the ratchet assembly is completely disengaged from the operation of the mechanical joint and has no influence on it, whereby the mechanical joint is freely movable between positions maximum extension and maximum flexion. Although not shown in FIGS. 1–8, such a position of ratchet assembly disengagement would be achieved in the most preferred embodiment of the present invention when the handle is moved closer to, or in contact with, first pivoting member 2.

Figure 5:
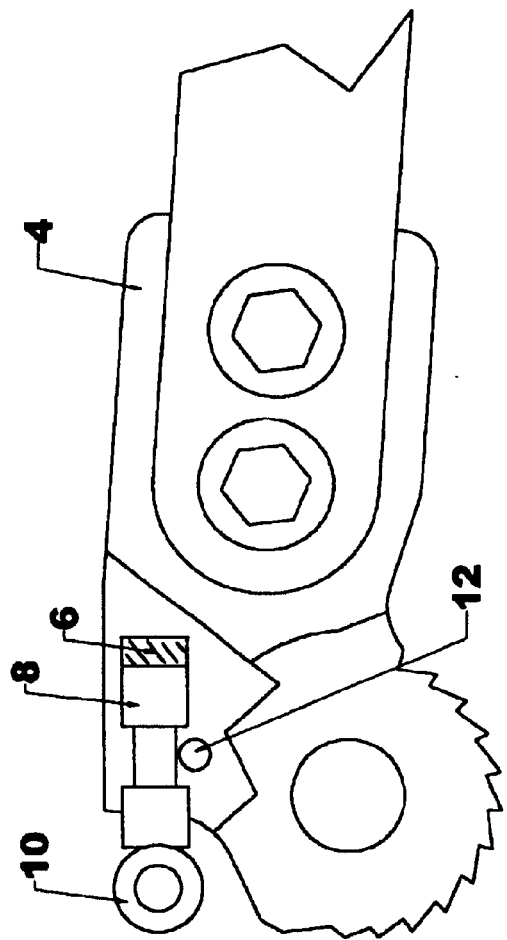
FIG. 5 is a side view of the most preferred embodiment of the present invention, with its retaining pin preventing removal of the piston from its usable position, the interior end of its piston in contact with a resilient bumper, and the opposing exposed end of the piston in contact with a cross stop bushing.
Figure 6:
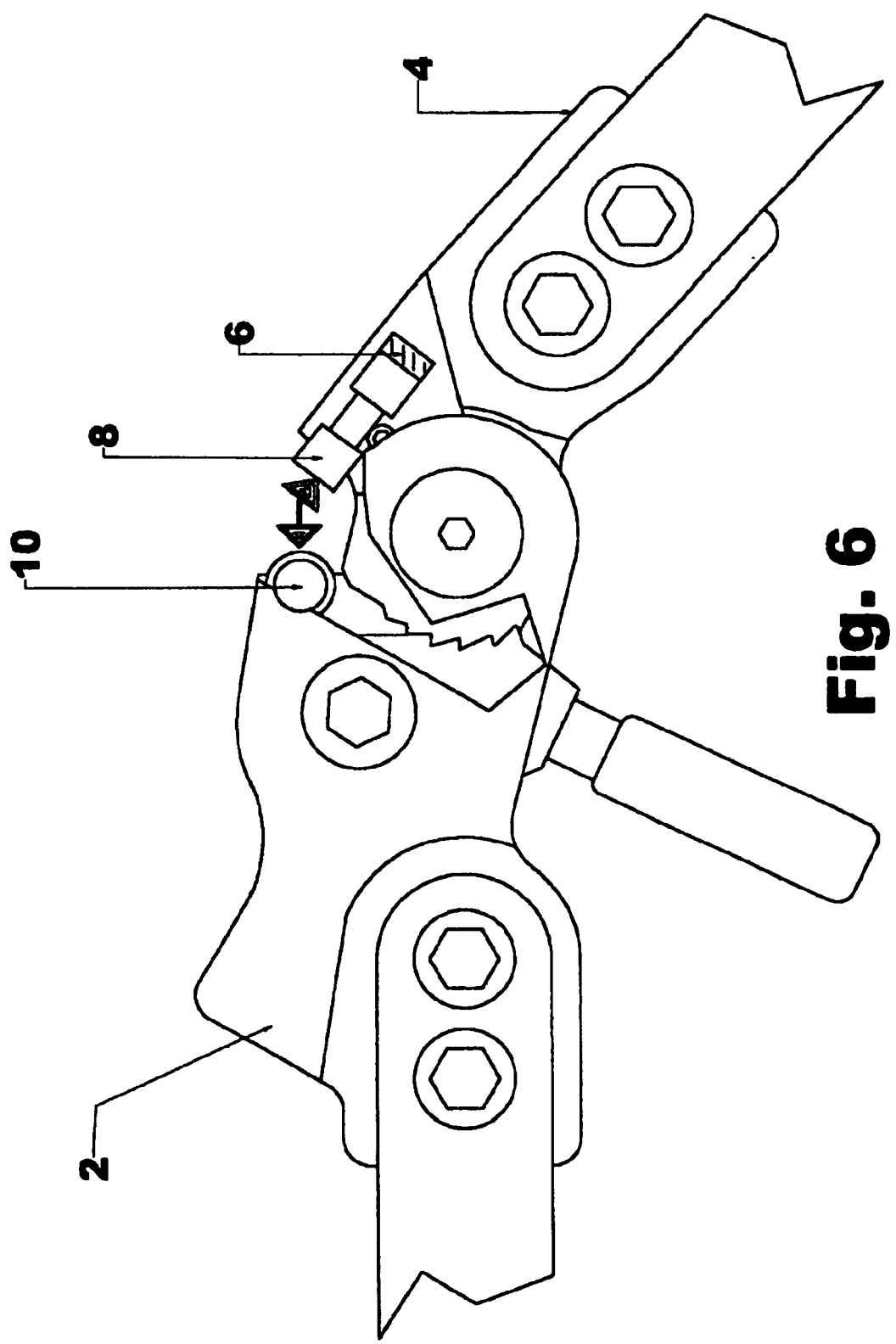
FIG. 6 is a side view of the most preferred embodiment of the present invention in a partially flexed mechanical joint that is locked against further flexion but capable of additional extension until the exposed end of the piston becomes fixed against the cross stop bushing, wherein a retaining pin prevents removal of the piston from its usable position in association with one of the pivoting members of a mechanical joint, the interior end of the piston is in contact with a resilient bumper, and arrows indicate a space between the exposed end of the piston and the cross stop bushing connected to the second pivoting member of the mechanical joint.
Figure 7:
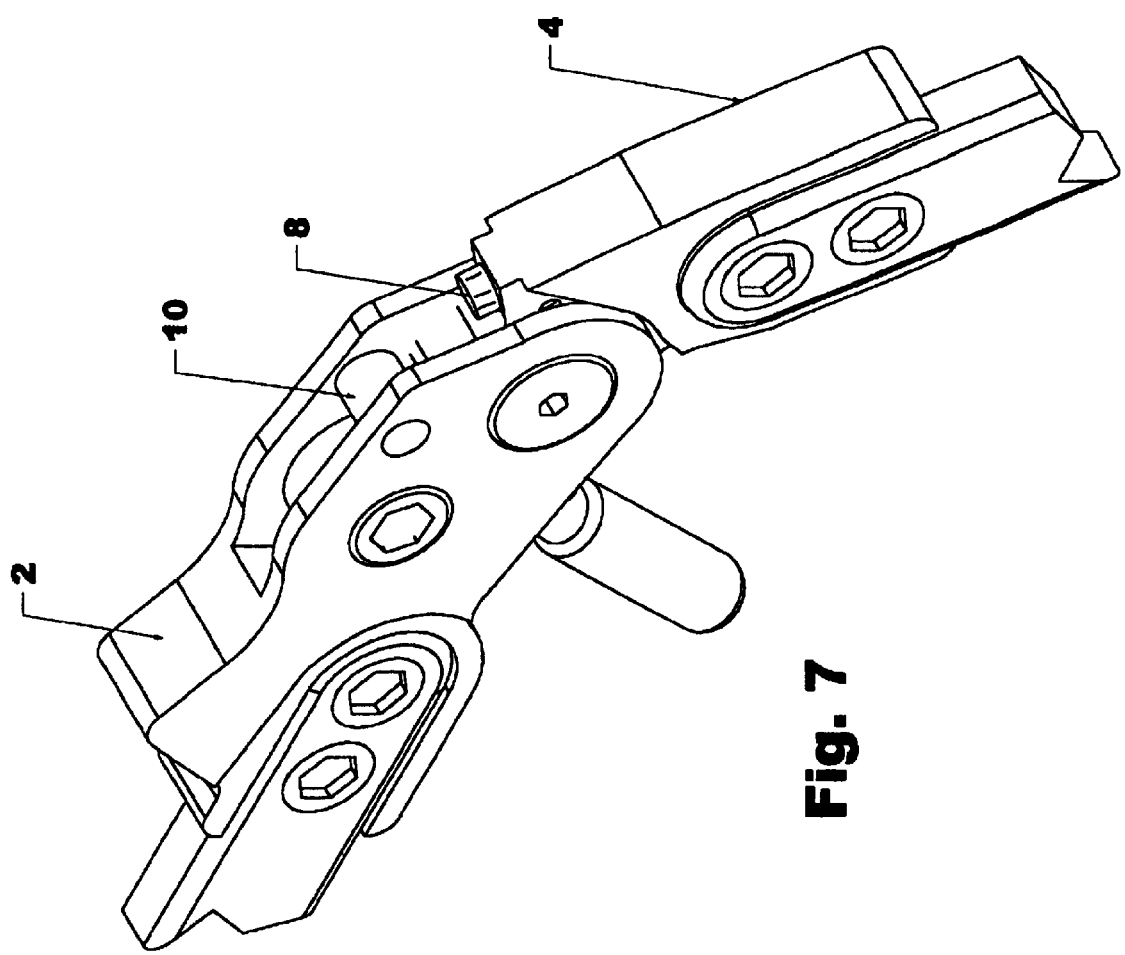
FIG. 7 is a perspective view of the most preferred embodiment of the present invention in a partially flexed mechanical joint that is locked against further flexion but capable of further extension, with a space shown between the exposed end of the piston and the cross stop bushing with which it engages to define a position of maximum extension for the mechanical joint.
Figure 8:
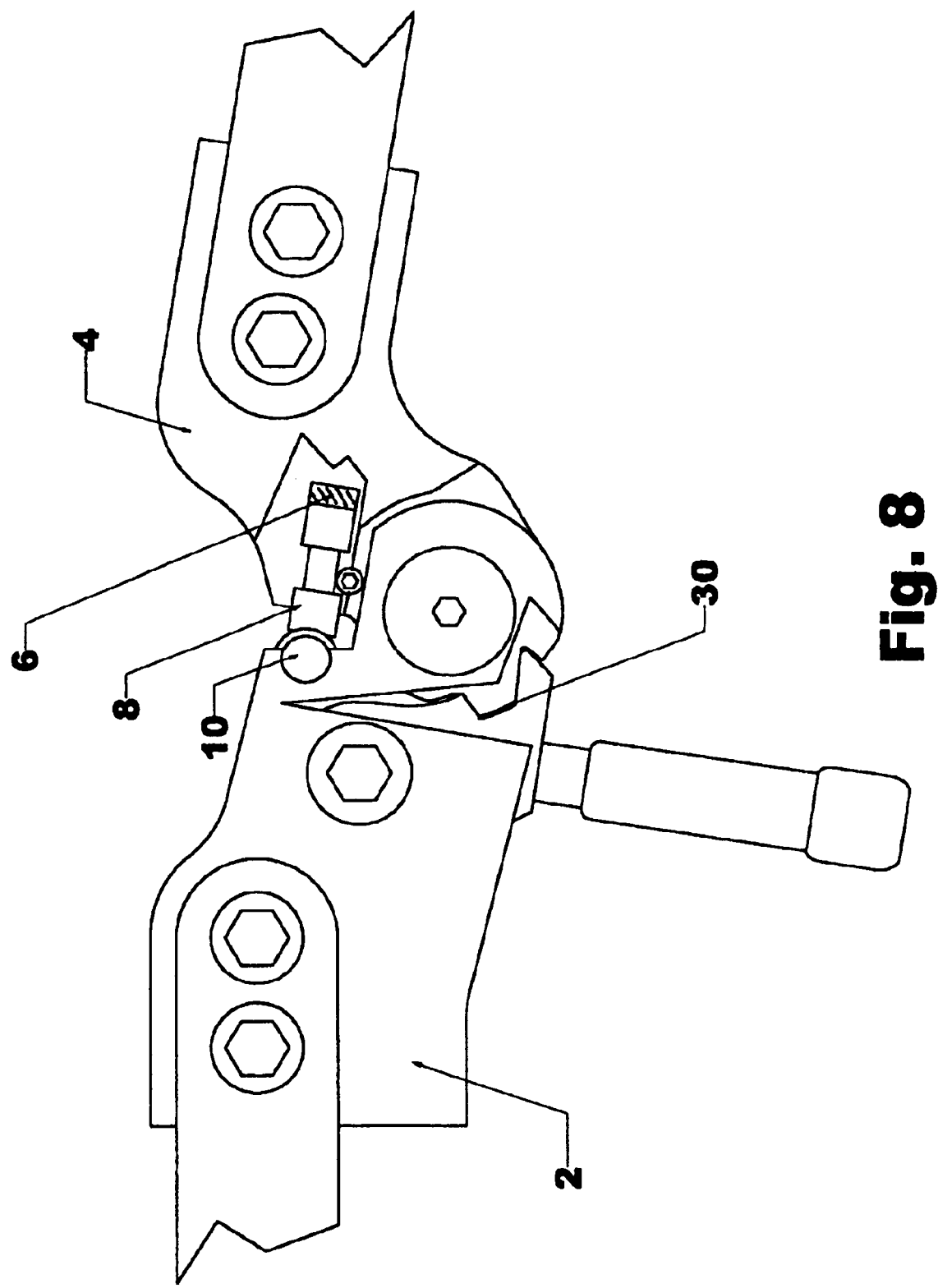
FIG. 8 is a partial sectional view of the most preferred embodiment of the present invention with its components laterally contained within a mechanical joint of a differing configuration and located so as to limit its extension, with the mechanical joint shown locked at a position of maximum extension, and also with the interior end of its piston in contact with a resilient bumper, a retaining pin defining the limits of longitudinal movement of the piston, and the piston, bumper, and retaining pin all connected to the same one of the pivoting members in the mechanical joint, and the exposed end of the piston in contact with a cross stop bushing connected to the other pivoting member in the mechanical joint.

FIGS. 1, 5, 6, and 7 show the present invention in association with the pivoting members of a first configuration of a mechanical joint, with first pivoting member 2 and second pivoting member 4 positioned on opposite sides of the pivoting axis of the joint and aligned with it. In FIGS. 1 and 5 the mechanical joint is in its position of maximum extension. In contrast, FIG. 8 shows a second configuration of a mechanical joint in which when the mechanical joint is in its position of maximum extension, with first pivoting member 2 and second pivoting member 4 being substantially aligned with piston 8, bumper 6, and cross stop bushing 10, instead of being aligned with the pivoting axis of the joint. Although alignment of first pivoting member 2 and second pivoting member 4 varies in FIGS. 1, 6, 7, and 8, the positioning of piston 8, bumper 6, cross stop bushing 10, and retaining pin 12 relative to the pivoting axis of the mechanical joint remains the same. However, it is not critical for retaining pin 12 to be restricted to a location between piston 8 and the pivoting axis of the mechanical joint, providing that there is sufficient space elsewhere within second pivoting member 4 to position retaining pin 12 so that it can maintain piston 8 within its longitudinally defined usable position. FIGS. 1, 5, and 8 show piston 8, bumper 6, and cross stop bushing 10 as they would appear when the mechanical joint is in its position of maximum extension. Conversely, FIGS. 6 and 7 show piston 8, bumper 6, and cross stop bushing 10 as they would appear when the mechanical joint is in its position of partial flexion. Further, in FIGS. 1, 6, 7, and 8, wherein the mechanical joint is in a position of partial flexion or a position of maximum extension, the unnumbered ratchet assembly that is not claimed as a part of the present invention is engaged so as to prevent further flexion, although in FIGS. 6 and 7 further extension in incremental amounts is permitted until the defined position of maximum extension is reached. Also, in FIGS. 1, 5, 6, 7, and 8, first pivoting member 2 and second pivoting member 4 are each shown connected by two fasteners (unnumbered) to a different side bar (also unnumbered).

Piston 8, cross stop bushing 10, and retaining pin 12 are preferably made from stainless steel, although not limited to such material. Also, retaining pin 12 can be a threaded set screw, or have no threads. The end configuration of retaining pin 12 can also allow for insertion of a tool that is able to easily withdraw retaining pin 12 from its usable position, and reinsert it, as needed. Bumper 10 can be made from a variety of flexible and/or resilient materials. However, bumper 10 should be made from a durable material for use during an extended period of time prior to replacement. Not withstanding the foregoing, preferred materials for bumper 10 include, but are not limited to, rubber, silicone, and urethane.

Figure 4:
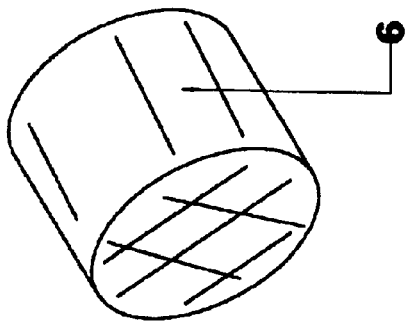
FIG. 4 is a perspective view of the resilient bumper in the most preferred embodiment of the present invention.
Figure 3:
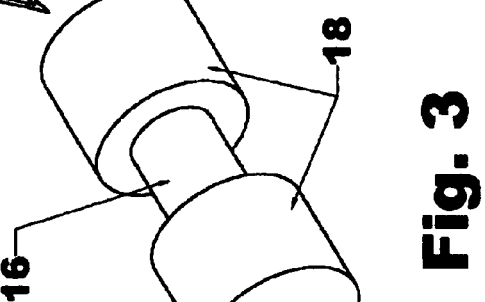
FIG. 3 is a perspective view of the configuration of the piston in the most preferred embodiment of the present invention.
Figure 2:
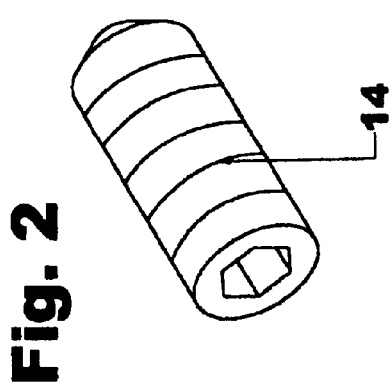
FIG. 2 is a perspective view of the retaining pin in the most preferred embodiment of the present invention used to maintain the piston in its usable position within a bore.

FIGS. 2, 3, and 4 respectively show an enlarged retaining pin 12, enlarged piston 8, and an enlarged cross stop bushing 10. Although the configurations show are those contemplated for use in the most preferred embodiment of the present invention, other configurations are also possible and contemplated, such as but not limited to pistons 8 having different length and/or different diameter dimensions, bumpers 6 with different thickness dimensions, more than one bumper 6 being used, pistons 8 having a different central configuration created for interaction with retaining pin 12, retaining pin 12 having a diameter dimension different from that shown, retaining pin 12 having different surface markings from that shown, and retaining pin 12 having a different end configuration from that shown. Also, although FIG. 4 shows the end configuration of bumper 6 to have a flat configuration, such configuration can also be arcuate, as can the end configuration of piston 8 in FIG. 3.

Thus, the present invention defines a position of maximum extension for first pivoting member 2 and second pivoting member 4 in the mechanical joint with which they are associated. Piston 8 and cross stop bushing 10 remain separated from one another at all times except when first pivoting member 2 and the second pivoting member 4 are very close to or pivoted into the position of maximum extension limited by the contact of the exposed end of piston 8 against cross stop bushing 10, with the interior end of piston 8 also pushing against resilient bumper 6. To use the preferred embodiment of the present invention shown in FIGS. 1–8 for orthotic use in support of a human knee, piston 8, cross stop bushing 10, and retaining pin 12 would be made from durable materials able to withstand without deterioration, for an extended period of time, the repeated stress caused by a load equivalent to the body weight of its heaviest anticipated user (not shown). Since cross stop bushing 10 is positioned within first pivoting member 2, and piston 8, retaining pin 12, and bumper 6 are all laterally contained within second pivoting member 4, the present invention does not add thickness dimension to the mechanical joint with which it is associated, and thereby can provide cosmetic and operational advantage.

What is claimed is:

1. A stop for a mechanical joint having a first pivoting member and a second pivoting member that, in addition to limiting the maximum extension of the joint, dampens free movement in the joint at full extension and provides a soft extension stop for the joint as it reaches maximum extension, said stop comprising:

a substantially cylindrical bore longitudinally situated within said second pivoting member, said bore having an open end and a closed end, with said closed end positioned remote from said first pivoting member;

a piston positioned and configured for movement within said bore, with a portion of said piston being capable of extending beyond said open end of said bore;

retaining pin means extending through said bore and adapted for prevention removal of said piston from said open end;

bumper means positioned between said piston and said closed end of said bore, said bumper means also adapted for elastic deformation so that deformation thereof can occur upon contact by said piston during each joint extension; and bushing means situated within said first pivoting member and adapted for engaging said portion of said piston extending beyond said open end of said bore during joint extension whereby at maximum extension of the mechanical joint said piston becomes fixed in place between said bumper means and said bushing means, and in close contact therewith.

2. The stop of claim 1 wherein said retaining pin means maintains said piston substantially within said bore.

3. The stop of claim 1 wherein said bore is situated within said second pivoting member so as to be located on the outside portion of the pivoting axis of the mechanical joint formed by the first and second pivoting members.

4. The stop of claim wherein piston has a central cutout area configured and positioned to engage said retaining pin means so that together said cutout area and said retaining pin means are able to limit the maximum distance said piston can move beyond said open end of said bore when the joint is not in its position of maximum extension.

5. The stop of claim 4 wherein said retaining pin means is positioned transversely to said piston.

6. The stop of claim wherein said retaining pin means comprises an end configuration allowing for insertion of a tool adapted for easy removal of said retaining pin means from its usable position.

7. The stop of claim 1 wherein said bushing means comprises a cross stop bushing.

8. The stop of claim 1 wherein said retaining pin means is positioned where it remains inaccessible and invisible until the pivoting members are separated from one another.

9. The stop of claim 1 wherein said bushing means and said piston are made from rigid and durable materials.

10. A stop for a mechanical joint having a first pivoting member, a second pivoting member, and a locking mechanism to prevent flexion of the joint, that in addition to limiting the maximum extension of the joint, dampens free movement in the joint at full extension, provides a larger increased tolerance in the range of motion for the locking mechanism to engage as the joint reaches maximum extension and provides a soft extension stop for the joint as it reaches maximum extension, said stop comprising:

a substantially cylindrical bore longitudinally situated within said second pivoting member, said bore having an open end and a closed end, with said closed end positioned remote from said first pivoting member;

a piston having a first end and an opposing second end, said piston being positioned within said bore and configured for free-floating movement therein, with said first end of said piston being adjacent to said closed end of said bore and said second end of said piston being capable of extending beyond said open end of said bore; a piston-retaining pin positioned through said bore so as to allow free-floating longitudinal movement of said piston within said bore while at the same time preventing removal of said piston from said bore;

bumper means adapted and positioned for engaging said first end of said piston and dampening the movement of said piston as it moves toward said closed end of said cylinder during joint extension; and bushing means situated within said first pivoting member and adapted for engaging said opposing second end of said piston during joint extension whereby at maximum extension of the mechanical joint said piston becomes fixed in place between said bumper means and said bushing means.

11. The stop of claim 10 wherein said piston-retaining yin maintains said piston substantially within said bore.

12. The stop of claim 10 wherein said piston has a central cutout area configured and positioned to engage said retaining pin so that together said cutout area and said retaining am are able to limit the maximum distance said piston can move beyond said open end of said bore when the joint is not in its position of maximum extension.

13. The stop of claim 12 wherein said piston-retaining pin is positioned transversely to said piston.

14. The stop of claim 10 wherein said piston-retaining pin comprises an end configuration allowing for insertion of a tool adapted for easy removal of said piston-retaining pin from its usable position.

15. The stop of claim 10 wherein said bushing means comprises a cross stop bushing.

16. The stop of claim 10 wherein said piston-retaining pin is positioned where it remains inaccessible and invisible until the pivoting members are separated from one another.

17. The stop of claim 10 wherein said bushing means and said piston are made from rigid arid durable materials.

18. The stop of claim 10 wherein said bumper means is made from resilient material, and said bushing means and said piston are made from rigid and durable materials.

19. A stop for a mechanical joint having two pivoting members and a pivoting axis therebetween, one pivoting member having a bore with an open end adjacent to the pivoting axis, which in addition to limiting maximum extension of the mechanical joint dampens free movement in the joint at full extension and provides a soft extension stop for the joint as it reaches maximum extension, said piston comprising:

a piston having a first end and an opposing second end, said piston also being positioned within the bore and substantially filling it, with said second end of said piston extending beyond the open end of the bore, said piston further having a central cutout area a piston-retaining pin positioned within the Pivoting member having the bore so as to engage said cutout area so as to allow free-floating longitudinal movement of said piston within the bore and prevent said piston from being removed from the bore when the joint is not at maximum extension;

bumper means adapted and positioned within the bore for engaging said first end of said piston, said bumper means also being adapted for elastic deformation so that deformation thereof can occur upon contact by said piston during each joint extension; and bushing means in the pivoting member without the bore and adapted for temporarily engaging said opposing second end of said piston during joint extension whereby at maximum extension of the mechanical joint said piston becomes fixed in place between said bumper means and said bushing means.

20. The stop of claim 19 wherein the pivoting members in the mechanical joint with which said stop is associated are selected from a group consisting of the pivoting members aligned with said piston, said bumper means, and said bushing means, and pivoting members aligned with the pivoting axis of the mechanical joint.

* * * * *